United States Patent
Giambattista et al.

(10) Patent No.: US 11,338,096 B2
(45) Date of Patent: *May 24, 2022

(54) MEDICAMENT INJECTION DEVICE

(71) Applicant: SHL MEDICAL AG, Zug (CH)

(72) Inventors: Lucio Giambattista, Lighthouse Point, FL (US); Slobodan Stefanov, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 339 days.

This patent is subject to a terminal disclaimer.

(21) Appl. No.: 16/585,059

(22) Filed: Sep. 27, 2019

(65) Prior Publication Data

US 2020/0023141 A1    Jan. 23, 2020

Related U.S. Application Data

(63) Continuation of application No. 15/528,374, filed as application No. PCT/EP2015/074465 on Oct. 22, 2015, now Pat. No. 10,493,215.

(30) Foreign Application Priority Data

Nov. 21, 2014    (SE) .................................... 1451407-9

(51) Int. Cl.
*A61M 5/32* (2006.01)
*A61M 5/315* (2006.01)
*A61M 5/20* (2006.01)

(52) U.S. Cl.
CPC .............. *A61M 5/326* (2013.01); *A61M 5/20* (2013.01); *A61M 5/31501* (2013.01);
(Continued)

(58) Field of Classification Search
CPC .. A61M 5/3243; A61M 5/3257; A61M 5/326; A61M 5/3265; A61M 5/3271; A61M 5/3272
See application file for complete search history.

(56) References Cited

U.S. PATENT DOCUMENTS 1,393,720 A * 10/1921 Lomas .............. A61M 5/31595
604/210
3,327,904 A * 6/1967 Goda .................. A61M 5/3158
222/309

(Continued)

FOREIGN PATENT DOCUMENTS

EP    1090652 A1    4/2001
GB    2463071 A     3/2010
(Continued)

*Primary Examiner* — William R Carpenter
(74) *Attorney, Agent, or Firm* — McDonnell Boehnen Hulbert & Berghoff LLP

(57) ABSTRACT

The present disclosure relates to a medicament injection device (1) comprising a housing (3) arranged to receive a medicament container (11*a*), a needle cover (9) movable relative to the housing (3), from a retracted position, in which it engages the housing (3) and enables medicament delivery, to an extended position, a plunger rod (7), and a plunger driver (5) movable relative to the housing (3) from all initial position to a final position, and arranged to actuate the plunger rod (7), wherein the plunger rod (7) has a first guide arrangement and the housing (3) has a second guide arrangement, the first guide arrangement (7*d*) and the second guide arrangement being arranged to cooperate to guide movement of the plunger rod (7) relative to the housing (3), wherein the first guide arrangement and the second guide arrangement in a first stage provide a linear motion path for the plunger rod (7), enabling the plunger rod (7) to initially move in the axial direction and in a second stage provide a rotation motion path for the plunger rod (7), enabling the plunger rod (7) to rotate relative to the housing (3) to release the plunger rod (7) from the plunger driver (5), whereby the plunger driver (5) attains a released state enabling movement of the plunger driver (5) to its final position, wherein in the released state the plunger driver (5) is arranged to (Continued)

release the needle cover (9) from the housing (3) and to actuate the needle cover (9) to its extended position.

20 Claims, 7 Drawing Sheets

(52) U.S. Cl.
CPC ...... *A61M 5/31583* (2013.01); *A61M 5/3202* (2013.01); *A61M 5/3243* (2013.01); *A61M 2005/3265* (2013.01)

(56) References Cited

U.S. PATENT DOCUMENTS

| | | | | |
|---|---|---|---|---|
| 5,163,918 | A * | 11/1992 | Righi | A61M 5/326 |
| | | | | 604/198 |
| 6,461,333 | B1 | 10/2002 | Frezza | |
| 6,712,793 | B1 | 3/2004 | Geiger et al. | |
| 8,105,292 | B2 * | 1/2012 | Verespej | A61M 5/326 |
| | | | | 604/192 |
| 10,493,215 | B2 * | 12/2019 | Giambattista | A61M 5/20 |
| 2014/0163476 | A1 * | 6/2014 | Chevallier | A61M 5/326 |
| | | | | 604/198 |
| 2017/0165423 | A1 * | 6/2017 | Holland | A61M 5/315 |

FOREIGN PATENT DOCUMENTS

| | | | |
|---|---|---|---|
| GB | 2546499 | A | 7/2017 |
| WO | 2012000838 | A2 | 1/2012 |
| WO | 2014139939 | A1 | 9/2014 |
| WO | 2017125732 | A1 | 7/2017 |

* cited by examiner

MEDICAMENT INJECTION DEVICE

CROSS REFERENCE TO RELATED APPLICATIONS

The present application is a continuation of U.S. patent application Ser. No. 15/528,374 filed May 19, 2017, which is a U.S. National Phase Application pursuant to 35 U.S.C. § 371 of International Application No. PCT/EP2015/074465 filed Oct. 22, 2015, which claims priority to Swedish Patent Application No. 1451407-9 filed Nov. 21, 2014. The entire disclosure contents of these applications are herewith incorporated by reference into the present application.

TECHNICAL FIELD

The present disclosure generally relates to medicament injection devices. In particular, it relates to a manual medicament injection device which provides needle protection after the completion of medicament injection.

BACKGROUND

Medicament injection devices are utilised to administer a medicament to a user. Medicament injection devices have a needle for injecting the medicament. The needle is covered prior to medicament delivery to assure that the needle is clean during medicament delivery. The needle is furthermore preferably covered also after medicament delivery to ensure that the used needle does not unintentionally scratch or pierce the skin of a person handling the medicament injection device after usage. Moreover, it is also desirable that the needle obtains this protected position post medicament administration automatically without the involvement of a user, to render the medicament injection device difficult to reuse.

An example of a medicament injection device that provides needle protection after medicament delivery is disclosed in EP1090652 B1. This document discloses a needle guard assembly for the needle part of a syringe body in the form of a needle guard which is longitudinally displaceable along the syringe body, and with a grip plate being integrally formed on a part of the syringe body remote from the needle. The needle guard assembly includes a syringe body ending with a needle. A piston rod in the syringe body has a receiving part and a push-in part that telescopes into the receiving part. A syringe-body grip plate is integrally formed on the syringe body. The syringe-body grip plate opposes the needle. The needle guard covers the needle when the needle guard is displaced longitudinally.

The solution disclosed in EP1090652 B1 relies on the push-in part telescoping into the receiving part after a catch-mounting is broken by applying a pressure on the grip plate above a predetermined value after the medicament has been injected. If a user for example has a disease which severely limits the user's strength, preventing the user from breaking the catch/mounting, it may result in that the needle guard will not cover the needle after injection.

SUMMARY

In view of the above, a general object of the present disclosure is to provide a medicament injection device which at least mitigates the problems of the prior art.

There is hence provided a medicament injection device comprising: a housing arranged to receive a medicament container, a needle cover movable relative to the housing, from a retracted position, in which it engages the housing and enables medicament delivery, to an extended position, a plunger rod, and a plunger driver movable relative to the housing from an initial position to a final position, and arranged to actuate the plunger rod, wherein the plunger rod has a first guide arrangement and the housing has a second guide arrangement, the first guide arrangement and the second guide arrangement being arranged to cooperate to guide movement of the plunger rod relative to the housing, wherein the first guide arrangement and the second guide arrangement in a first stage provide a linear motion path for the plunger rod, enabling the plunger rod to initially move in the axial direction and in a second stage provide a rotation motion path for the plunger rod, enabling the plunger rod to rotate relative to the housing to release the plunger rod from the plunger driver, whereby the plunger driver attains a released state enabling movement of the plunger driver to its final position, wherein in the released state the plunger driver is arranged to release the needle cover from the housing and to actuate the needle cover to its extended position.

By being able to actuate the needle cover to its extended position by means of the plunger driver, a needle extending from the housing may be fully covered, with essentially no additional force than the amount of force utilised for injecting the medicament. Therefore, also users afflicted by reduced strength, but who are able to inject the medicament, may also be able to push the plunger driver to the final position.

According to one embodiment the plunger driver has a final position-maintaining arrangement configured to lock the plunger driver to the housing in the final position, hence locking the needle cover in the extended position. Therefore, the needle cover cannot be moved back towards the retracted position without resorting to excessive force that could damage the medicament injection device. A needle extending from the housing is thus safely protected after medicament injection. This may be especially advantageous for disposable medicament injection devices.

According to one embodiment the final position-maintaining arrangement includes a snap-mechanism arranged to engage a shoulder on the internal surface of the housing.

According to one embodiment the plunger driver is arranged to release the needle cover by movement of the plunger driver towards the final position.

According to one embodiment in the initial position the plunger driver engages with the plunger rod to enable actuation of the plunger rod.

According to one embodiment the needle cover has a first blocking arrangement and the housing has a second blocking arrangement, wherein the first blocking arrangement is arranged to engage the second blocking arrangement in the extended position of the needle cover to prevent the needle cover from sliding out of the housing.

According to one embodiment the first guide arrangement is a groove.

According to one embodiment the second guide arrangement is a protrusion slidably arranged in the groove.

According to one embodiment the plunger driver has a central rod extending coaxially in a central opening of the plunger rod, wherein an outer surface of the central rod has a plunger rod engagement arrangement and a surface of the central opening has a central rod engagement arrangement, wherein the plunger rod engagement arrangement and the central rod engagement arrangement are arranged to be engaged along the linear motion path and arranged to disengage along the rotation motion path.

According to one embodiment the needle cover has a housing engagement arrangement arranged to engage the housing in the retracted position.

According to one embodiment the housing engagement arrangement comprises a flexible tongue and a heel arranged at the tip of the flexible tongue, wherein the inner surface of the housing has a first cut-out arranged to receive the heel.

According to one embodiment the heel has a proximal end surface arranged to abut a proximal wall defining the first cut-out, thereby retaining the needle cover in the retracted position.

According to one embodiment the heel has a distal end and a proximal end, wherein the heel has a thickness that gradually increases in a direction from the distal end towards the proximal end.

According to one embodiment the plunger driver has a proximal end arranged to slide onto the heel to bend the flexible tongue away from the housing to thereby release the needle cover from the housing.

One embodiment comprises a medicament container and needle, wherein the in the extended position the needle cover is arranged to cover the needle. Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Throughout this text, with "proximal" end is meant that end of a component which is closest to the tip of the needle. With "distal" end is meant the opposite end of a component relative to the proximal end. Thus, for example, the proximal end of the medicament injection device is that end which is directed towards a user during injection.

Figure 1:
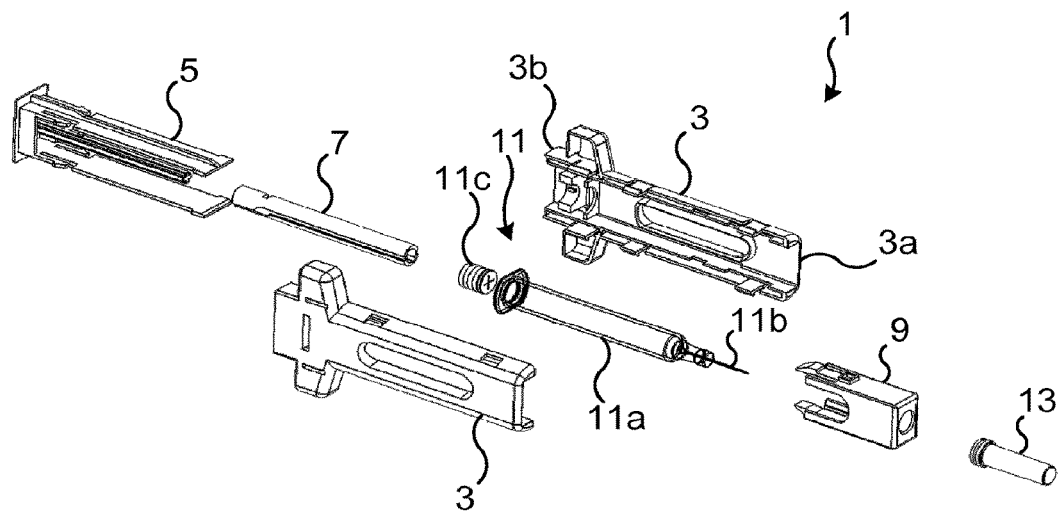
FIG. 1 is an exploded view of a medicament injection device.

FIG. 1 is an exploded view of an example of a medicament injection device 1, which according to the example includes a medicament container assembly. The medicament injection device 1 comprises a housing 3 having a proximal end 3a and a distal end 3b, and according to the example including two halves arranged to be assembled to form the housing 3, a plunger driver 5, a plunger rod 7, and a needle cover 9.

The medicament injection device 1 may further comprise a medicament container assembly 11 including a medicament container 11a, which may contain a medicament, a needle 11b, and a stopper 11c. When the medicament injection device 1 is in an assembled state, and comprising the medicament container assembly 11, the needle 11b protrudes from the proximal end 3a of the housing 3.

The medicament injection device 1 may further comprise a removable needle shield 13, for example a rigid needle shield (RNS), arranged to protect the needle 11b prior to medicament injection.

The plunger driver 5 and the plunger rod 7 are arranged to be received by the housing 3. The plunger driver 5 is arranged to move axially relative to the housing 3 from an initial position, in which the plunger driver 5 has a maximal extension from the distal end 3b of the housing 3, to a final position in which it is maximally received by the housing 3.

The plunger driver 5 is arranged to actuate the plunger rod 7. The plunger driver 5 therefore engages the plunger rod 7 in the initial position. Thus, when the plunger driver 5 is moved from the initial position towards the final position, the plunger rod 7 is actuated by the plunger driver 5 and follows the motion of the plunger driver 5. The plunger rod 7 is arranged to actuate the stopper 11c such that the stopper 11c is moved longitudinally in the medicament container 11a towards the needle 11b, allowing medicament to be expelled through the needle 11b.

The needle cover 9 is arranged to be received by the housing 3. The needle cover 9 is arranged to move from a retracted position in which it allows medicament delivery from the medicament container 11a, provided that the needle shield 13 is removed from the needle 11b, to an extended position. In the extended position the needle 11b is covered by the needle cover 9. Initially, when the plunger driver 5 is in the initial position, the needle cover 9 engages the housing 3 so as to maintain its retracted position.

The plunger rod 7 and the housing 3 are arranged to interact to provide a two-stage motion path for the plunger rod 7 when actuated by the plunger driver 5. In the first stage a linear motion path is provided, enabling the plunger rod 7 to initially move solely in the axial direction. In a second stage a rotation motion path is provided, enabling the plunger rod 7 to rotate relative to the housing 3. In the second stage the plunger rod 7 disengages the plunger driver 5 and the plunger driver 5 is thus released from the plunger rod 7. As a result, the plunger driver 5 attains a released state enabling the plunger driver to be moved to the final position.

In the released state, the plunger driver 5 can be further pushed into the housing 3. In the released state, the plunger driver 5 is arranged to disengage or decouple the needle cover 9 from the housing 3 as the plunger driver 5 is moved towards its final position. The plunger driver 5 is furthermore arranged to actuate the needle cover 9 to the retracted position when the plunger driver 5 is moved towards the final position. The needle cover 9 attains the extended position when the plunger driver 5 attains the final position.

In the final position, the plunger driver 5 engages the housing 3 to maintain the final position. Thereby, the needle cover 9 maintains the extended position and the needle 11b is thus protected post medicament delivery.

Figure 2A:
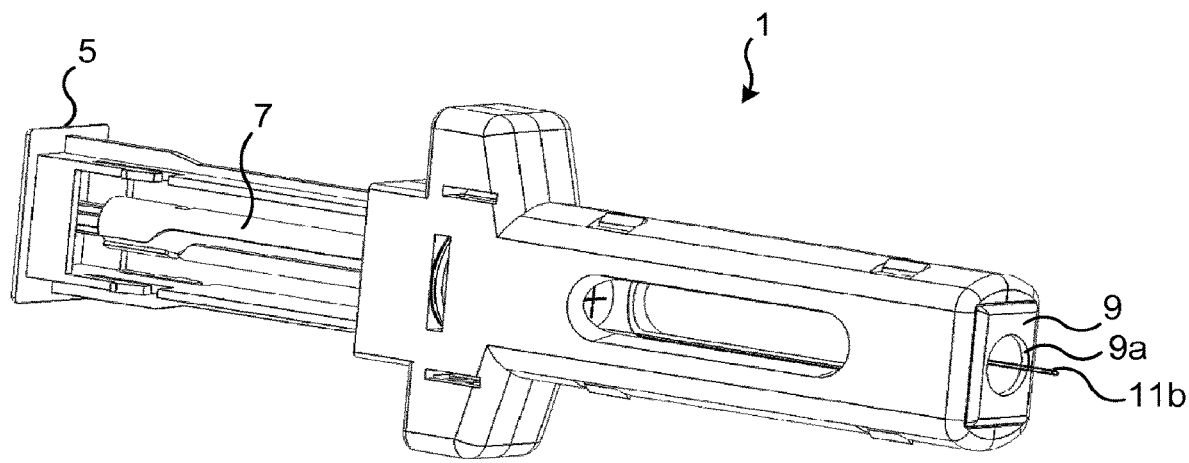
FIGS. 2a-2c show the medicament injection device in FIG. 1 in various states.
Figure 2B:
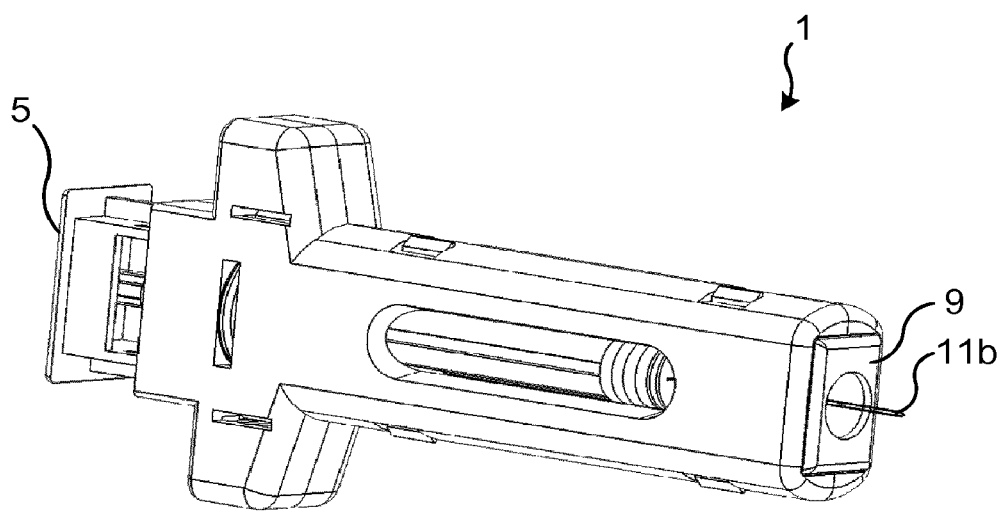
Figure 2C:
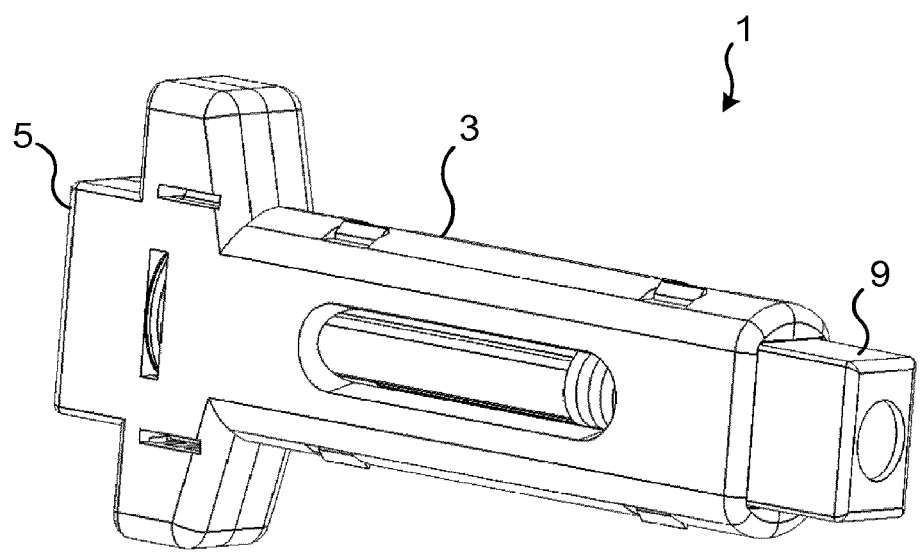

FIGS. 2a-2c shows the medicament injection device 1 in different states. In FIG. 2a, the medicament injection device 1 is shown prior to medicament delivery, when the plunger driver 5 is in the initial position, the needle cover 9 is in the retracted position and the needle shield is removed. The needle cover 9 has a central opening 9a through which the needle 11b extends.

In FIG. 2b, the medicament injection device 1 is shown in a state in which a medicament has been expelled by the needle 11b. The plunger driver 5 is in a position between the initial position and the final position. The needle cover 9 is still in the retracted position. When the plunger driver 5 is pushed further inwards into the housing 3, the plunger driver 5 is disengaged or decoupled from the plunger rod 7 to attain the released state so that the plunger driver can cooperate with the needle cover 9 to disengage the needle cover 9 from the housing and to actuate the needle cover to the extended position.

In FIG. 2c, the medicament injection device 1 is shown in a final state, after medicament injection and when the plunger driver 5 is in the final position and the needle cover 9 is in the extended position. The needle cover 9 hence covers the needle, and the plunger driver 5 engages the housing 3 to maintain the final position.

Figure 3:
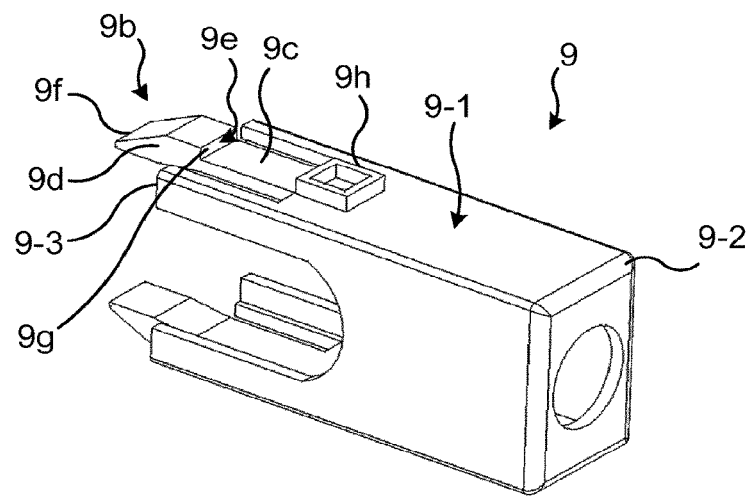
FIG. 3 is a perspective view of a needle cover of the medicament injection device in FIG. 1.

FIG. 3 is a perspective view of the needle cover 9, which has a main body 9-1, a proximal end 9-2 and a distal end 9-3. The needle cover 9 has a housing engagement arrangement 9b arranged to engage the housing 3 when the needle cover 9 is in the retracted position. According to the example shown in FIG. 3 the housing engagement arrangement 9b comprises a flexible tongue 9c and a heel 9d arranged at the tip of the flexible tongue 9c. The flexible tongue 9c extends from the main body 9-1 in a direction from the proximal end 9-2 towards the distal end 9-3.

Figure 6:
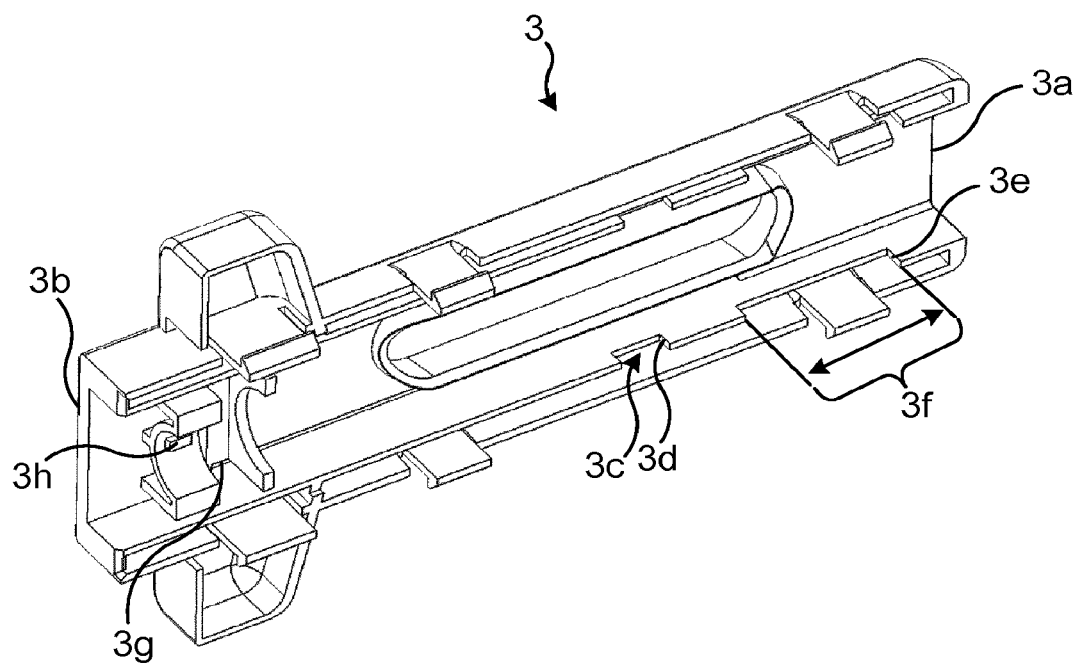
FIG. 6 is a perspective view of an inner side of a housing of the medicament injection device in FIG. 1.

The heel 9d has a proximal end surface 9e arranged to engage with the housing 3. As shown in FIG. 6, the housing 3 has a first cut-out 3c in which the heel 9d is arranged to be received when the needle cover 9 is in the retracted position. The first cut-out 3c has a proximal wall 3d against which the proximal end surface 9e of the heel 9d abuts. The needle cover 9 can thereby be retained in the in the retracted position prior to medicament delivery.

The heel 9d has a distal end 9f and a proximal end 9g. The heel 9d has a thickness that gradually increases in a direction from the distal end 9f towards the proximal end 9g. The heel 9d may preferably by wedge-shaped. The plunger driver 5 has a proximal end 5a, which when the plunger driver 5 is in the released state and is pushed inwards further into the housing 3, slides onto the wedge-shaped heel 9d, bending the flexible tongue 9c inwards in a direction away from the inner surface of the housing 3. The needle cover 9 is thus released from the first cut-out 3c of the housing 3 enabling the needle cover 9 to slide towards the extended position.

The needle cover 9 has a first blocking arrangement 9h and the housing 3 has a second blocking arrangement 3e, as shown in FIG. 6. The first blocking arrangement 9h is arranged to engage or abut the second blocking arrangement 3e in the extended position of the needle cover 9 to prevent the needle cover 9 from sliding out of the housing 3. The first blocking arrangement 9h comprises a protrusion and the second blocking arrangement 9h comprises a second cut-out 3f which has a longitudinal extension larger than the axial extension of the protrusion and which is arranged to receive the protrusion. The proximal end wall and distal end wall defining the second cut-out 3f hence provide a play for the protrusion. When the needle cover 9 is in the retracted position the protrusion is arranged at a distal end wall of the second cut-out 3f, and when the needle cover 9 is in the extended position, the protrusion abuts the proximal end wall of the second cut-out 3f. The needle cover 9 is thus blocked from further extension relative to the proximal end 3a of the housing 3.

As an alternative to the above-described configuration, the needle cover could have a first cut-out and the housing could have a flexible tongue and a heel arranged to be received by the needle cover, wherein the proximal end of the plunger driver 5 could cooperate with the heel of the housing instead, to release the needle cover from the housing. Similarly, the housing could instead be provided with the first blocking arrangement and the needle cover could be provided with the second blocking arrangement.

Figure 4:
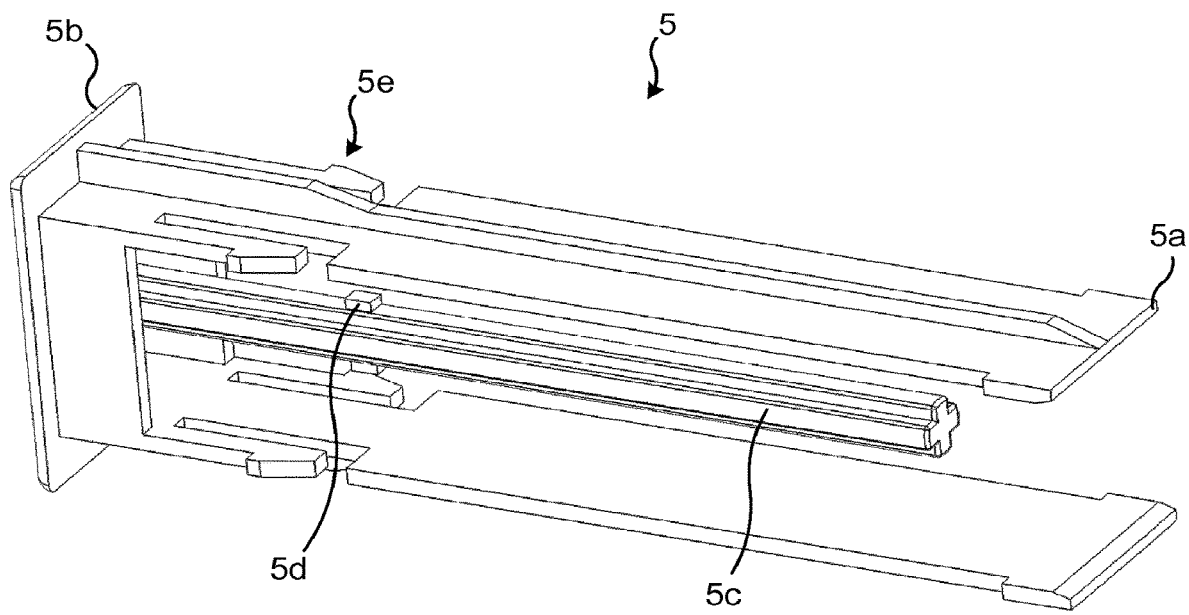
FIG. 4 is a perspective view of a plunger driver of the medicament injection device in FIG. 1.

FIG. 4 is a perspective view of an example of a plunger driver 5. The plunger driver 5 has a proximal end 5a and a distal end 5b. The exemplified plunger driver 5 comprises a central rod 5c arranged to extend into a central opening of the plunger rod 7. The central rod 5c extends coaxially in the central opening of the plunger rod 7. The outer surface of the central rod 5c has a plunger rod engagement arrangement 5d. According to the example, the plunger rod arrangement 5d comprises two protrusions, elevated in opposite directions. The plunger rod engagement arrangement 5d is arranged to engage the surface of the central opening of the plunger rod 7 in the initial position of the plunger driver 5, and while the plunger rod 7 moves along a linear motion path. When the plunger rod 7 is rotated in a rotation motion path the plunger rod arrangement 5d disengages the plunger rod 7, releasing the plunger driver 5 from the plunger rod 7.

Figure 5A:
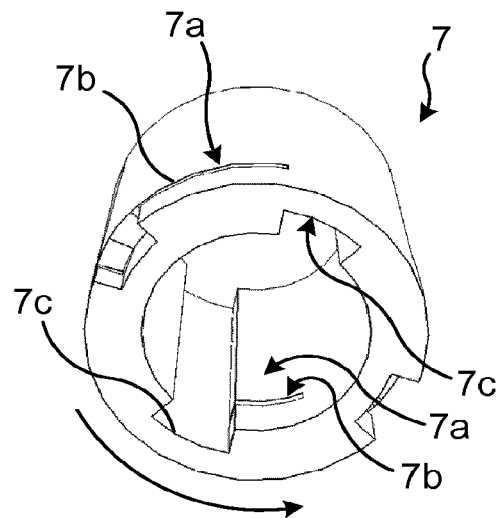
FIGS. 5a-5b are perspective view of the a plunger rod of the medicament injection device in FIG. 1.

FIG. 5a shows the plunger rod 7. The plunger rod 7 has a central rod engagement arrangement 7a arranged to cooperate with the plunger rod engagement arrangement 5d. The central rod engagement arrangement 7a comprises two slits 7b disposed at 180° from each other, and arranged to receive a respective one of the protrusions of the plunger rod engagement arrangement 5d. When the plunger rod 7 is rotated, the protrusions of the plunger rod engagement arrangement 5d slide out from the slits 7b, into a respective longitudinal groove 7c arranged along the inner surface of the central opening of the plunger rod 7. The plunger driver 5 is thus disengaged from the plunger rod 7, enabling additional movement of the plunger driver 5 into the housing 3 even when the stopper 11c has reached its end position in which the entire medicament dose has been expelled through the needle 11b, and in which the plunger rod 7 also has reached an end position.

The housing 3 is arranged to cooperate with the plunger rod 7, in order to enable linear motion and rotational motion of the plunger rod 7 when actuated by the plunger driver 5.

Figure 5B:
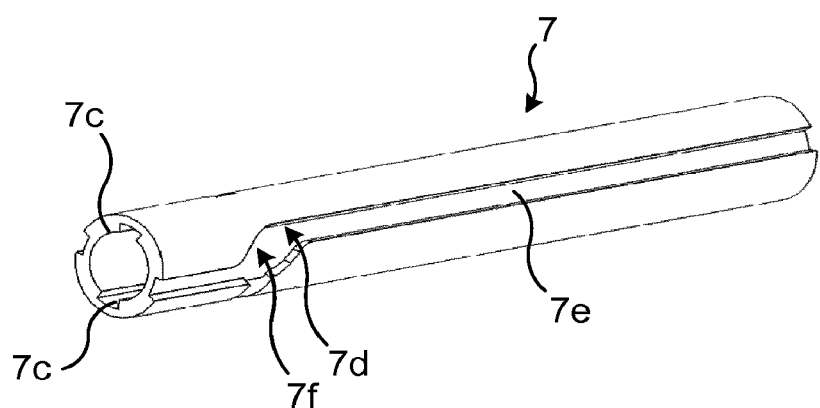

With reference to FIG. 5b a perspective view of the plunger rod 7 is shown. The plunger rod 7 has a first guide arrangement 7d. The housing 3 has a second guide arrangement 3h, as shown in FIG. 6. The first guide arrangement 7d and the second guide arrangement 3h are arranged to cooperate, to guide the movement of the plunger rod 7 relative to the housing 3 when actuated by the plunger driver 5. The first guide arrangement 7d and the second guide arrangement 3h are arranged to in a first stage to provide a linear motion path for the plunger rod 7 enabling the plunger rod 7 to initially move in the axial direction. The first guide arrangement 7d and the second guide arrangement 3h are arranged to in a second stage provide a rotation motion path for the plunger rod 7 enabling the plunger rod 7 to rotate relative to the housing 3, and relative to the central rod 5c.

According to the example in FIGS. 5b and 6, the first guide arrangement 7d is a groove arranged in the outer surface of the plunger rod 7 and the second guide arrangement 3h is a protrusion slidably arranged in the groove. According to the example, the groove has a linear motion path portion 7e and a rotation motion path portion 7f. The groove hence changes direction along the outer surface of the plunger rod 7. Thus, when the second guide arrangement 3h slides along the groove and enters the rotation motion path portion 7f, the plunger rod 7 rotates relative to the housing 3, and relative to the central rod 5c, such that the central rod engagement arrangement 5d disengages from the plunger rod engagement arrangement 5d and decouples the plunger driver 5 from the plunger rod 7.

Returning to FIG. 4, the plunger driver 5 comprises a final position-maintaining arrangement 5e arranged to engage the housing 3 in the final position of the plunger driver 5 to maintain the plunger driver 5 in the final position. According to the example, the final position-maintaining arrangement 5e comprises a snap-mechanism arranged to engage a shoulder 3g on the inner surface of the housing 3, as shown in FIG. 6.

Figure 7:
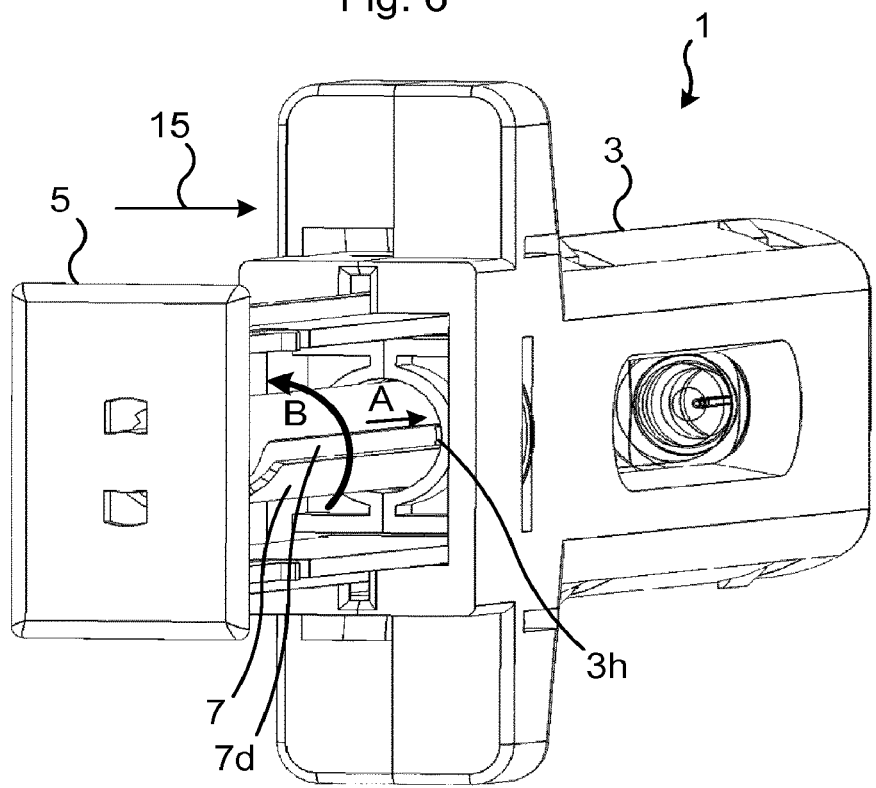
FIG. 7 is a perspective view of the rear side of a medicament injection device.
Figure 8:
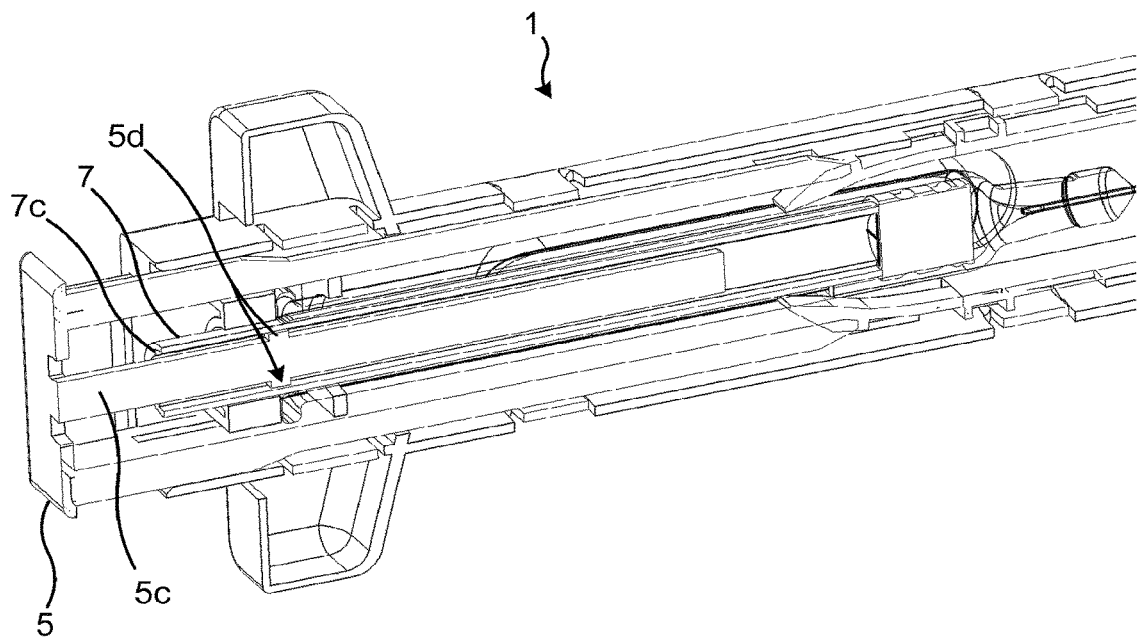
FIG. 8 is a sectional view along the central axis of a medicament injection device.

FIG. 7 shows the medicament injection device 1 when the plunger driver 5 is in the initial position. It can be seen that the second guide arrangement 3h engages the first guide arrangement 7d, i.e. the protrusion is arranged in the groove. As the plunger driver 15 is pushed into the housing 3 in the direction shown by arrow 15, the protrusion will slide along the groove. The plunger rod 7 will thus move linearly as shown by arrow A until the groove changes direction in the rotation motion path portion 7f. As the groove changes direction, and the protrusion slides along the rotation motion path portion 7f, the plunger rod 7 will rotate in the direction shown by arrow B, disengaging the plunger driver 5. This is shown in the section of the medicament injection 3o device 1 shown in FIG. 8, where it can be seen that the plunger rod engagement arrangement 5d slides into the longitudinal groove 7c, enabling the plunger driver 5 to move axially relative to the plunger rod 7.

The central rod 5c does not extend all the way to the bottom of the central opening of the plunger rod 7 when the plunger driver 5 attains the released state, enabling the central rod 5c to be moved further into the central opening when the plunger driver 5 continues to be pushed towards the final position.

Figure 9:
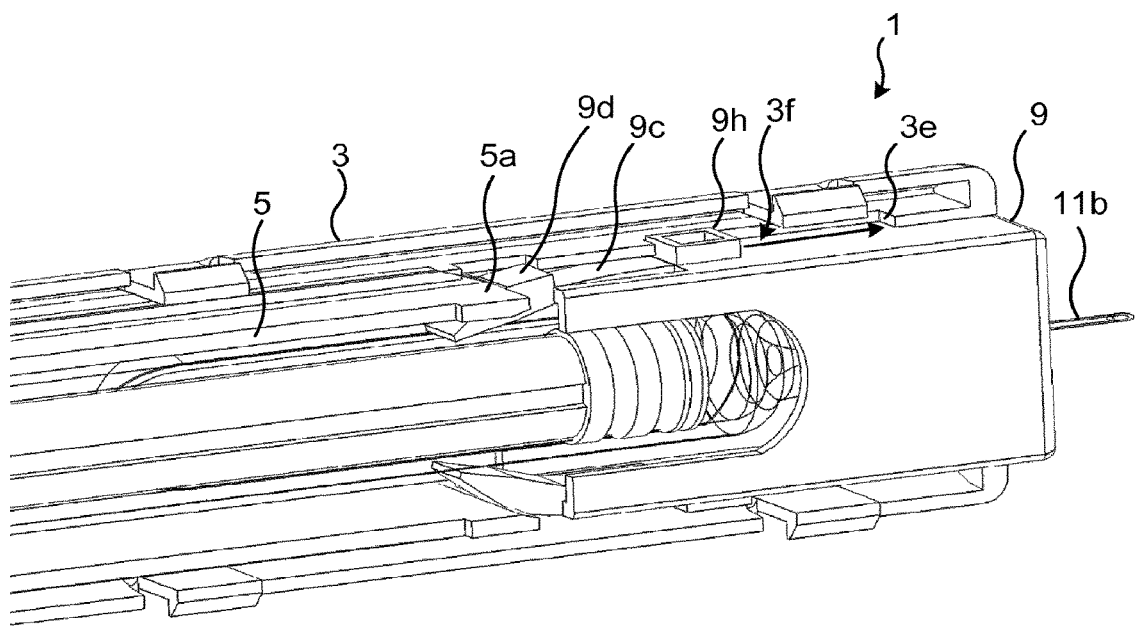
FIGS. 9 and 10 show the decoupling and blocking of the needle cover.
Figure 10:
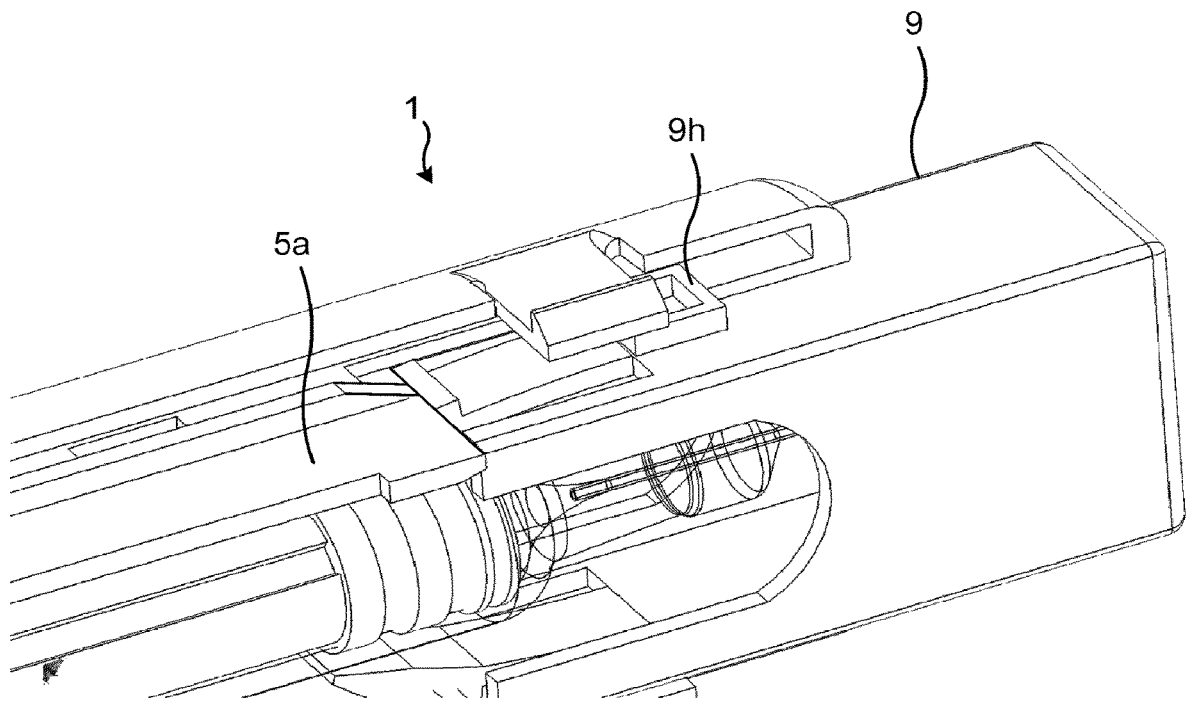

FIG. 9 shows a proximal portion of the medicament injection device 1, with its interior exposed. The proximal end 5a of the plunger driver 5 has slid onto the sloping surface of the wedge-shaped heel 9d. As the plunger driver 5 is pushed further towards its final position, the flexible tongue 9c is bent away from the inner surface of the housing 3, towards the centre axis of the housing 3. The needle cover 9 is thus released from its engagement with the housing 3, enabling the needle cover 9 to be moved axially until the first blocking arrangement 9h reaches and abuts the second blocking arrangement 3e, i.e. the protrusion abuts the proximal end wall of the second cut-out 3f. This situation is illustrated in FIG. 10, in which the needle cover 9 has reached its extended position. The first blocking arrangement 9h and the second blocking arrangement 3e prevent the needle cover 9 from sliding out from the housing 3.

Figure 11:
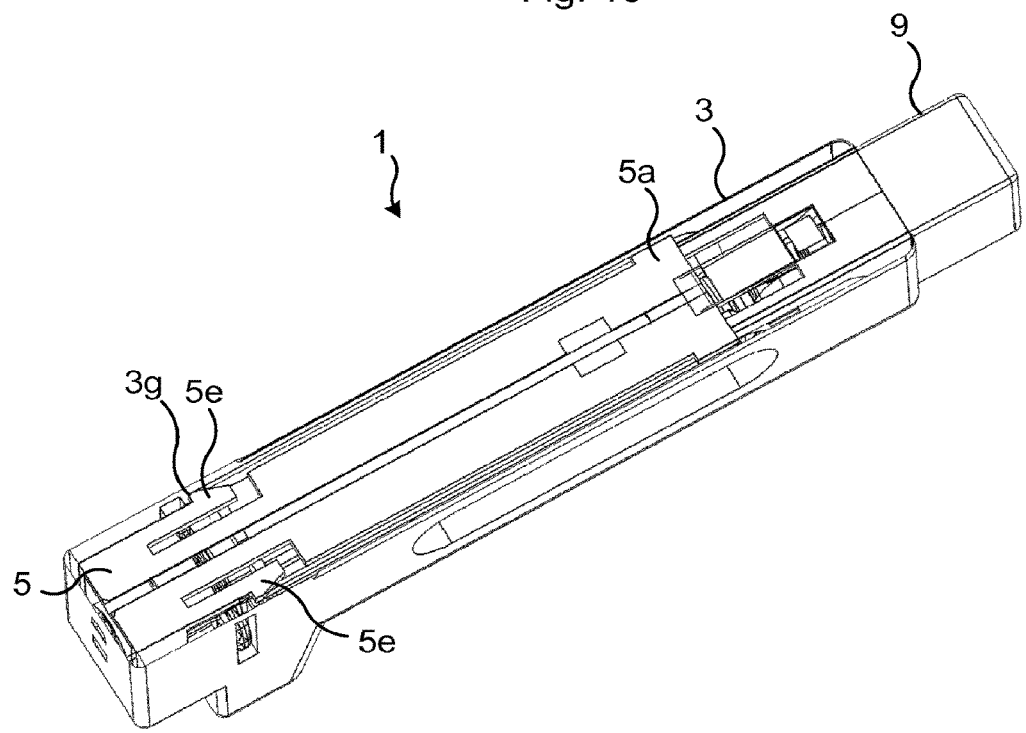
FIG. 11 is a section of a medicament injection device depicting engagement of a final position-maintaining arrangement of the plunger driver with the housing.

FIG. 11 shows a sectional view of the medicament injection device 1 when the plunger driver 5 is in the final position and the needle cover 9 is in the extended position. The final position-maintaining arrangement 5e of the plunger driver 5 is engaged with the shoulder 3g of the housing 3, resulting in that the plunger driver 5 cannot be removed from housing 3. The needle cover 9 is thus locked into its extended position, because the proximal end 5a of the plunger driver 5 abuts the heel 5d preventing the needle cover 9 from movement towards its retracted position.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament injection device comprising:
a housing comprising a shoulder;
a needle cover movable relative to the housing from a retracted position to an extended position;
a plunger rod slidably and rotationally engaged with the housing along a linear motion path and a rotation motion path such that the plunger rod first moves linearly and then rotates relative to the housing during medicament delivery, and
a plunger driver movable relative to the housing from an initial position to a final position and arranged to actuate the plunger rod, the plunger driver comprising an arrangement configured to engage the shoulder when the plunger driver is in the final position to maintain the needle cover in the extended position,
wherein proximal movement of the plunger driver to the final position is initially relative to the needle cover until the plunger driver engages the needle cover to cause the needle cover to move proximally from the retracted position and to disengage from the housing and to move the extended position,
wherein a portion of the plunger driver is engaged with inside surface of the plunger rod and where the rotation of the plunger rod disengages the plunger rod from the plunger driver such that the plunger driver can move axially relative to the plunger rod.

2. The medicament injection device of claim 1, wherein the shoulder is positioned at a distal end of the housing and the arrangement is positioned at a distal end of plunger driver.

3. The medicament injection device of claim 1, wherein the arrangement being engaged with the shoulder is further configured to maintain the plunger driver in the final position.

4. The medicament injection device of claim 1, wherein the arrangement includes a snap-mechanism.

5. The medicament injection device of claim 1, wherein the shoulder is on an inner surface of the housing.

6. The medicament injection device of claim 1, wherein the plunger driver is arranged to release the needle cover by movement of the plunger driver towards the final position.

7. The medicament injection device of claim 1, wherein the needle cover has a first blocking arrangement and the housing has a second blocking arrangement.

8. The medicament injection device of claim 7, wherein the first blocking arrangement is configured to engage the second blocking arrangement when the needle cover is in the extended position to prevent the needle cover from sliding out of the housing.

9. The medicament injection device of claim 1,
wherein the plunger rod has a first guide arrangement and the housing has a second guide arrangement, the first guide arrangement and the second guide arrangement being arranged to cooperate to guide movement of the plunger rod relative to the housing, and
wherein the first guide arrangement and the second guide arrangement in a first stage provide the linear motion path for the plunger rod, enabling the plunger rod to move in an axial direction relative to the housing and in a second stage provide the rotational motion path for the plunger rod, enabling the plunger rod to rotate relative to the housing to release the plunger rod from the plunger driver.

10. The medicament injection device of claim 9, wherein the first guide arrangement is a groove and the second guide arrangement is a protrusion slidably arranged in the groove.

11. The medicament injection device of claim 10, wherein the plunger driver has a central rod extending coaxially in a central opening of the plunger rod.

12. The medicament injection device of claim 11, wherein an outer surface of the central rod has a plunger rod engagement arrangement and a surface of the central opening has a central rod engagement arrangement.

13. The medicament injection device of claim 12, wherein the plunger rod engagement arrangement and the central rod engagement arrangement are arranged to be engaged along the linear motion path and arranged to disengage along the rotation motion path.

14. The medicament injection device of claim 1, wherein the needle cover has a housing engagement arrangement arranged configured to engage the housing in the retracted position.

15. The medicament injection device of claim 14,
wherein the housing engagement arrangement comprises a flexible tongue and a heel arranged at a tip of the flexible tongue, and
wherein an inner surface of the housing has a first cut-out arranged to receive the heel.

16. The medicament injection device of claim 15, wherein the heel has a proximal end surface arranged to abut a proximal wall defining the first cut-out, thereby retaining the needle cover in the retracted position.

17. The medicament
injection device of claim 16, wherein the heel has a distal end and a proximal end, and
wherein the heel has a thickness that gradually increases in a direction from the distal end towards the proximal end.

18. The medicament injection device of claim 17, wherein the plunger driver has a proximal end arranged to slide onto the heel to bend the flexible tongue away from the housing to thereby release the needle cover from the housing.

19. The medicament injection device of claim 1, comprising a medicament container and a needle, wherein in the extended position the needle cover is arranged to cover the needle.

20. The medicament injection device of claim 1, wherein the needle cover enables medicament delivery when the needle cover is in the retracted position.

* * * * *